(12) United States Patent
Quintanar

(10) Patent No.: US 12,303,633 B2
(45) Date of Patent: *May 20, 2025

(54) CHANGING THERAPY DEVICES OR WOUND DRESSINGS IN REDUCED PRESSURE WOUND THERAPY

(71) Applicant: T.J.Smith and Nephew, Limited, Hull (GB)

(72) Inventor: Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,575

(22) Filed: May 7, 2024

(65) Prior Publication Data

US 2024/0285848 A1 Aug. 29, 2024

Related U.S. Application Data

(63) Continuation of application No. 17/312,775, filed as application No. PCT/EP2019/084609 on Dec. 11, 2019, now Pat. No. 11,992,602.

(30) Foreign Application Priority Data

Dec. 14, 2018 (GB) .................................. 1820388

(51) Int. Cl.
*A61M 1/00* (2006.01)

(52) U.S. Cl.
CPC ............ *A61M 1/985* (2021.05); *A61M 1/966* (2021.05); *A61M 1/98* (2021.05); *A61M 1/96* (2021.05);
(Continued)

(58) Field of Classification Search
CPC .... A61M 1/962; A61M 1/98; A61M 2205/14; A61M 1/00; A61M 1/90; A61M 1/96
See application file for complete search history.

(56) References Cited

U.S. PATENT DOCUMENTS

| | | |
|---|---|---|
| 7,678,090 B2 | 3/2010 | Risk, Jr. et al. |
| 7,763,000 B2 | 7/2010 | Risk, Jr. et al. |

(Continued)

FOREIGN PATENT DOCUMENTS

| | | |
|---|---|---|
| EP | 2648793 A1 | 10/2013 |
| EP | 3187205 A1 | 7/2017 |

(Continued)

OTHER PUBLICATIONS

International Appl. No. PCT/EP2019/084609, International Search Report and written opinion mailed Apr. 7, 2020, 12 pages.

(Continued)

*Primary Examiner* — Sarah Al Hashimi
*Assistant Examiner* — Meagan Ngo
(74) *Attorney, Agent, or Firm* — Knobbe, Martens, Olson & Bear, LLP

(57) ABSTRACT

An apparatus for applying negative pressure to a wound is disclosed. The apparatus can include a housing, a pressure source, a canister, and a controller. The pressure source can be supported by the housing and provide negative pressure via a fluid flow path to a wound dressing positioned over a wound. The canister can collect exudate from the wound. The controller can monitor a parameter indicative of providing negative pressure to the wound dressing with the pressure source, determine from the parameter that the wound is treatable with a canisterless wound therapy apparatus, and output for presentation to a user a notification indicating that the wound is treatable with the canisterless wound therapy apparatus.

20 Claims, 12 Drawing Sheets

(52) U.S. Cl.
CPC ............. *A61M 1/962* (2021.05); *A61M 1/982* (2021.05); *A61M 1/984* (2021.05); *A61M 2205/3327* (2013.01); *A61M 2205/3334* (2013.01); *A61M 2205/3553* (2013.01); *A61M 2205/581* (2013.01); *A61M 2205/582* (2013.01); *A61M 2205/583* (2013.01)

(56) References Cited

U.S. PATENT DOCUMENTS

| | | |
|---|---|---|
| 7,811,269 B2 | 10/2010 | Boynton et al. |
| 8,105,295 B2 | 1/2012 | Blott et al. |
| 8,167,869 B2 | 5/2012 | Wudyka |
| 8,235,972 B2 | 8/2012 | Adahan |
| 8,294,586 B2 | 10/2012 | Pidgeon et al. |
| 8,366,692 B2 | 2/2013 | Weston et al. |
| 8,377,016 B2 | 2/2013 | Argenta et al. |
| 8,444,392 B2 | 5/2013 | Turner et al. |
| 8,494,349 B2 | 7/2013 | Gordon |
| 8,663,200 B2 | 3/2014 | Weston et al. |
| 8,734,425 B2 | 5/2014 | Nicolini |
| 8,785,059 B2 | 7/2014 | Hartwell |
| 8,814,841 B2 | 8/2014 | Hartwell |
| 8,834,451 B2 | 9/2014 | Blott et al. |
| 8,843,327 B2 | 9/2014 | Vernon-Harcourt et al. |
| 8,845,603 B2 | 9/2014 | Middleton et al. |
| 8,852,149 B2 | 10/2014 | Weston et al. |
| 8,852,170 B2 | 10/2014 | Weston et al. |
| 8,945,074 B2 | 2/2015 | Buan et al. |
| 8,951,235 B2 | 2/2015 | Allen et al. |
| 8,974,429 B2 | 3/2015 | Gordon et al. |
| 9,067,003 B2 | 6/2015 | Buan et al. |
| 9,084,845 B2 | 7/2015 | Adie et al. |
| 9,227,000 B2 | 1/2016 | Fink et al. |
| 9,408,954 B2 | 8/2016 | Gordon et al. |
| 9,427,505 B2 | 8/2016 | Askem et al. |
| 9,526,817 B2 | 12/2016 | Blott et al. |
| 9,642,950 B2 | 5/2017 | Hartwell |
| 9,737,649 B2 | 8/2017 | Begin et al. |
| 9,901,664 B2 | 2/2018 | Askem |
| 10,155,070 B2 | 12/2018 | Childress et al. |
| 10,328,188 B2 | 6/2019 | Deutsch et al. |
| 2006/0129137 A1 | 6/2006 | Lockwood et al. |
| 2007/0118096 A1 | 5/2007 | Smith et al. |
| 2009/0299306 A1 | 12/2009 | Buan |
| 2011/0015593 A1 | 1/2011 | Svedman et al. |
| 2012/0001762 A1 | 1/2012 | Turner et al. |
| 2014/0058344 A1 | 2/2014 | Toth |
| 2017/0053073 A1 | 2/2017 | Allen et al. |

FOREIGN PATENT DOCUMENTS

| | | | |
|---|---|---|---|
| EP | 3127024 B1 | 9/2018 | |
| EP | 3893954 A1 | 10/2021 | |
| WO | WO-2009151645 A2 | 12/2009 | |
| WO | WO-2012078784 A1 | 6/2012 | |
| WO | WO-2016018448 A1 | 2/2016 | |
| WO | WO-2017027850 A1 * | 2/2017 | ............. A61F 13/00 |
| WO | WO-2018150263 A1 | 8/2018 | |
| WO | WO-2018164803 A1 | 9/2018 | |
| WO | WO-2018195101 A1 | 10/2018 | |
| WO | WO-2018210692 A1 | 11/2018 | |
| WO | WO-2018210693 A1 | 11/2018 | |
| WO | WO-2018231878 A1 | 12/2018 | |

OTHER PUBLICATIONS

International Preliminary Report on Patentability and Written Opinion for Application No. PCT/EP2019/084609, mailed on Jun. 24, 2021, 10 pages.

* cited by examiner

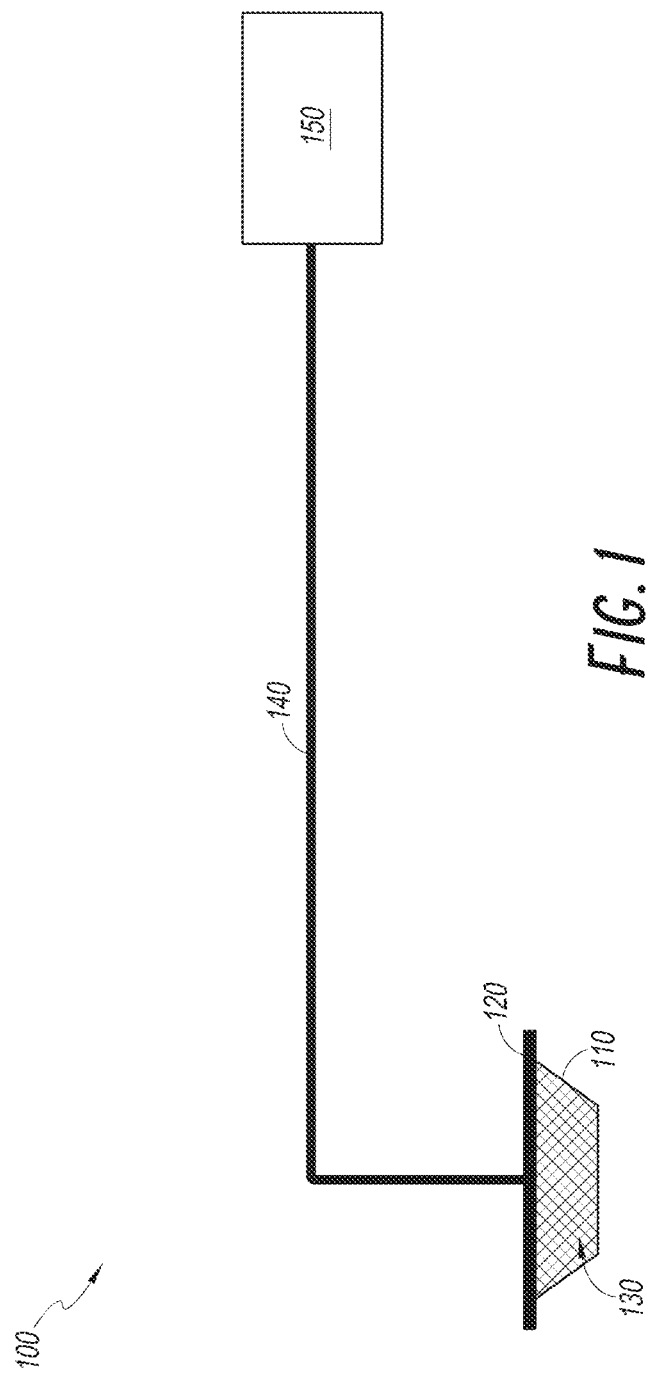

CHANGING THERAPY DEVICES OR WOUND DRESSINGS IN REDUCED PRESSURE WOUND THERAPY

CROSS-REFERENCE TO RELATED APPLICATIONS

This application is a continuation of U.S. application Ser. No. 17/312,775, filed Jun. 10, 2021, which is a U.S. national stage application of International Patent Application No. PCT/EP2019/084609, filed Dec. 11, 2019, which claims priority to U.K. Provisional Application No. 1820388.5 filed on Dec. 14, 2018; the disclosure of each of which is hereby incorporated by reference in its entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some aspects, an apparatus is disclosed for applying negative pressure to a wound. The apparatus can include a housing, a pressure source, a canister, and a controller. The pressure source can be supported by the housing and provide negative pressure via a fluid flow path to a wound dressing positioned over a wound. The canister can be in fluid communication with the wound dressing via the fluid flow path and collect fluid from the wound. The controller can: monitor a parameter indicative of providing negative pressure to the wound dressing with the pressure source, determine from the parameter that the wound is treatable with a canisterless wound therapy apparatus, and output for presentation to a user a notification indicating that the wound is treatable with the canisterless wound therapy apparatus.

The apparatus of the preceding paragraph can include one or more of the following features: The parameter can include one or more of a duration of therapy delivered with the pressure source, a pressure in the fluid flow path, a flow rate in the fluid flow path, a blockage in the fluid flow path, a fill amount of the wound dressing, a level of activity of the pressure source, a fill amount of the canister, a depth of the wound, or a frequency of exudate collection. The apparatus can include a sensor that detects the parameter. The controller can determine from a change in the parameter over time that the wound is treatable with the canisterless wound therapy apparatus. The controller can determine from a comparison of the parameter to a threshold that the wound is treatable with the canisterless wound therapy apparatus. The canister can be supported by the housing. The canisterless wound therapy apparatus can include an accompanying pressure source and be to operate in combination with an accompanying wound dressing that has a different fluid capacity than the wound dressing. The notification can include a visual indication, an audio indication, or a tactile indication. The apparatus can include a display supported by the housing and present the notification. The controller can determine a forecast of exudate collection from the wound and output the forecast for presentation to the user. The controller can update a profile for the user in response to determining that the wound is treatable with the canisterless wound therapy apparatus. The parameter can include a flow rate in the fluid flow path and a pressure in the fluid flow path, and the controller can determine that the wound is treatable with the canisterless wound therapy apparatus from a comparison of the flow rate in the fluid flow path to a flow threshold and from a comparison of a difference between the pressure in the fluid flow path and a pressure setting to a pressure threshold. The controller can determine that the wound is treatable with the canisterless wound therapy apparatus further from information received about a patient that has the wound. The controller can determine from the parameter that the wound dressing is full of the fluid. The controller can output the notification wirelessly to an electronic device.

A method of manufacturing or operating the apparatus of the preceding two paragraphs is disclosed.

In some aspects, a method of operating a wound therapy device is disclosed. The method can include: collecting, by a canister in fluid communication via a fluid flow path with a wound dressing positioned over a wound, fluid from the fluid flow path; monitoring a parameter indicative of providing negative pressure to the wound dressing with a pressure source; determining from the parameter that the wound is treatable with a canisterless wound therapy apparatus; and outputting for presentation to a user a notification indicating that the wound is treatable with the canisterless wound therapy apparatus.

The method of the preceding paragraph can include one or more of the following features: The parameter can include one or more of a duration of therapy delivered with the pressure source, a pressure in the fluid flow path, a flow rate in the fluid flow path, a blockage in the fluid flow path, a fill amount of the wound dressing, a level of activity of the pressure source, a fill amount of the canister, a depth of the wound, or a frequency of exudate collection. The method can further include detecting the parameter with a sensor. The determining can include determining from a change in the parameter over time that the wound is treatable with the canisterless wound therapy apparatus. The determining can include determining from a comparison of the parameter to a threshold that the wound is treatable with the canisterless wound therapy apparatus.

BRIEF DESCRIPTION OF THE DRAWINGS

Features and advantages of the present disclosure will be apparent from the following detailed description, taken in conjunction with the accompanying drawings of which:

FIG. 1 illustrates a wound therapy system.

DETAILED DESCRIPTION

Figure 2A:
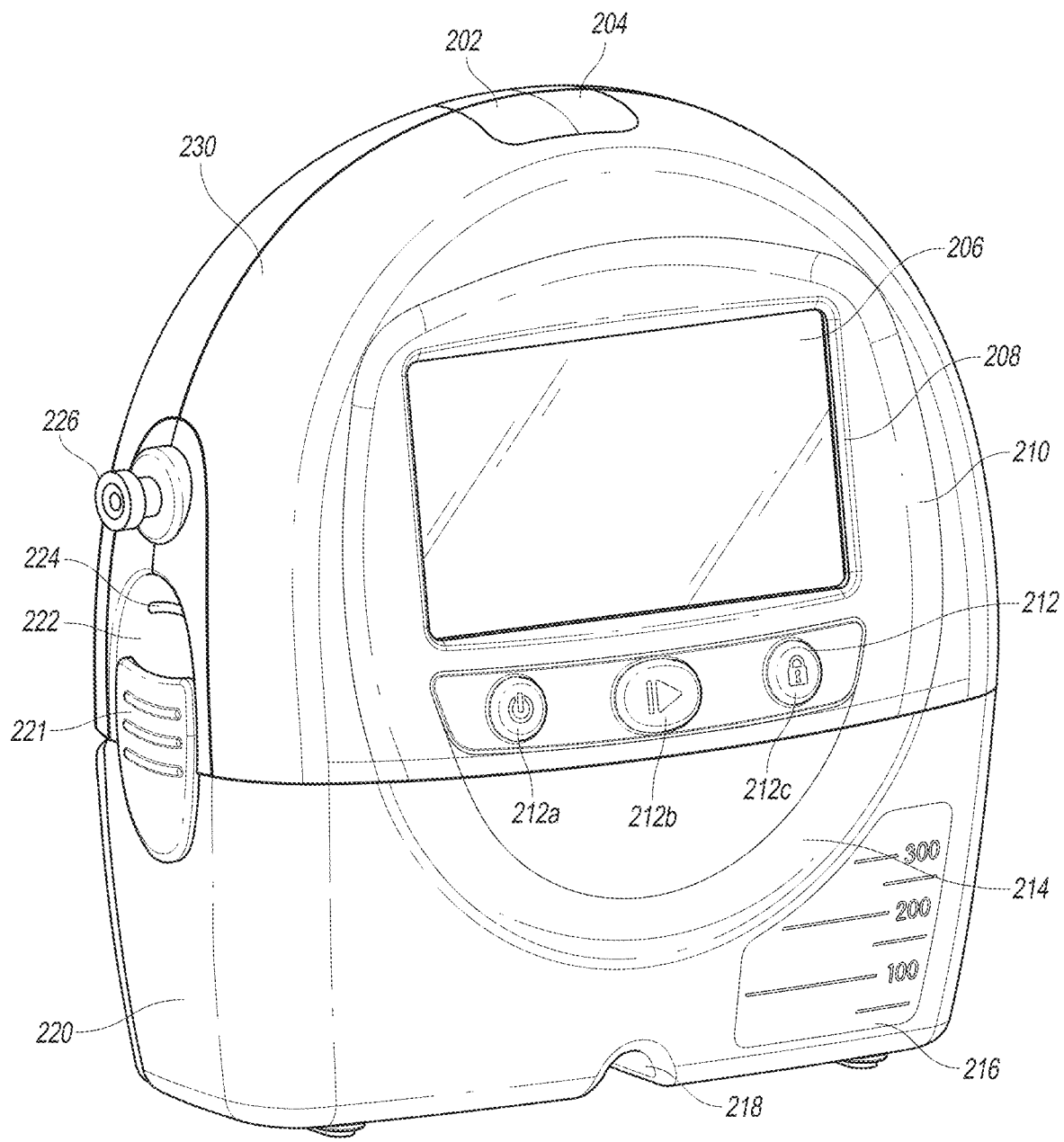
FIGS. 2A, 2B, and 2C illustrate a pump assembly and a canister.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as –X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of –X mmHg reflects pressure that is X mmHg below atmospheric pressure, such as a pressure of (760-X) mmHg. In addition, negative pressure that is "less" or "smaller" than-X mmHg corresponds to pressure that is closer to atmospheric pressure (for example, –40 mmHg is less than –60 mmHg). Negative pressure that is "more" or "greater" than-X mmHg corresponds to pressure that is further from atmospheric pressure (for example, –80 mmHg is more than –60 mmHg).

FIG. 1 illustrates a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connects the wound cover 120 with a pump assembly 150 configured to supply reduced pressure. The wound cover 120 can be in fluidic communication with the wound cavity 110.

In the systems disclosed herein, the pump assembly 150 can be a canisterless pump assembly (which, in addition to its ordinary meaning, may mean that exudate removed by the canisterless pump assembly is collected in a wound dressing and not by an accompanying canister used for collecting exudate) or be used in combination with a canister for collecting exudate removed by the pump assembly 150. Additionally, the pump assembly can be mounted to or supported by the wound dressing, or adjacent to the wound dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some implementations of the wound cover 120 can have a port (not shown) configured to receive an end of the conduit 140. For example, the port can be Renays Soft Port available from Smith & Nephew. In other implementations, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some aspects, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps can also be used.

The wound cover 120 can be located over a wound site to be treated. The wound cover 120 can form a substantially sealed cavity or enclosure over the wound site. In some aspects, the wound cover 120 can be configured to have a film having a high water vapor permeability to enable the evaporation of surplus fluid, and can have a super absorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

In some aspects, configuring the pump assembly 150 and conduit 140 so that the conduit 140 can be quickly and easily removed from the pump assembly 150 can facilitate or improve the process of dressing or pump changes, if necessary. The pumps disclosed herein can be configured to have any suitable connection between the tubing and the pump.

The pump assembly 150 can be configured to deliver negative pressure of approximately –80 mmHg, or between about –20 mmHg and –200 mmHg in some implementations. Note that these pressures are relative to normal ambient atmospheric pressure thus, –200 mmHg would be about 560 mmHg in practical terms. The pressure range can be between about –40 mmHg and –150 mmHg. Alternatively a pressure range of up to –75 mmHg, up to –80 mmHg or over –80 mmHg can be used. Also a pressure range of below –75 mmHg can be used. Alternatively a pressure range of over approximately −100 mmHg, or even −150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (for example, wound exudate) may be drawn into the wound cover 120, the wound filler 130, or another absorbent layer (not shown) and stored or through the conduit 140 and stored in a canister.

Wound dressings that may be utilized with the pump assembly and other aspects of the present application include Renasys-F, Renasys-G, Renasys AB, and Pico Dressings available from Smith & Nephew. Further description of such wound dressings and other components of a negative pressure wound therapy system that may be used with the pump assembly and other aspects of the present application are found in U.S. Patent Publication Nos. 2011/0213287, 2011/0282309, 2012/0116334, 2012/0136325, and 2013/0110058, which are incorporated by reference in their entirety. In other aspects, other suitable wound dressings can be utilized.

FIG. 2A illustrates a front view of a pump assembly 230 and canister 220 As is illustrated, the pump assembly 230 and the canister 220 are connected, thereby forming a wound therapy device. The pump assembly 230 can be similar to or the same as the pump assembly 150.

The pump assembly 230 includes one or more indicators, such as indicator 202 configured to visually indicate alarms and an indicator 204 configured to visually indicate status of the TNP system. The indicators 202 and 204 can be configured to alert a user, such as patient or medical care provider, to a variety of operating or failure conditions, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can include additional indicators. The pump assembly 230 can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other aspects, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. As illustrated, two latch recesses 222 can be formed on the sides of the pump assembly 230. The latch recesses 222 can be configured to allow attachment and detachment of the canister 220 or another canister using one or more latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. Two strap mounts 226 can be formed on the sides of the pump assembly 230. In some aspects, various of these features are omitted or various additional features are added to the pump assembly 230.

Figure 5:
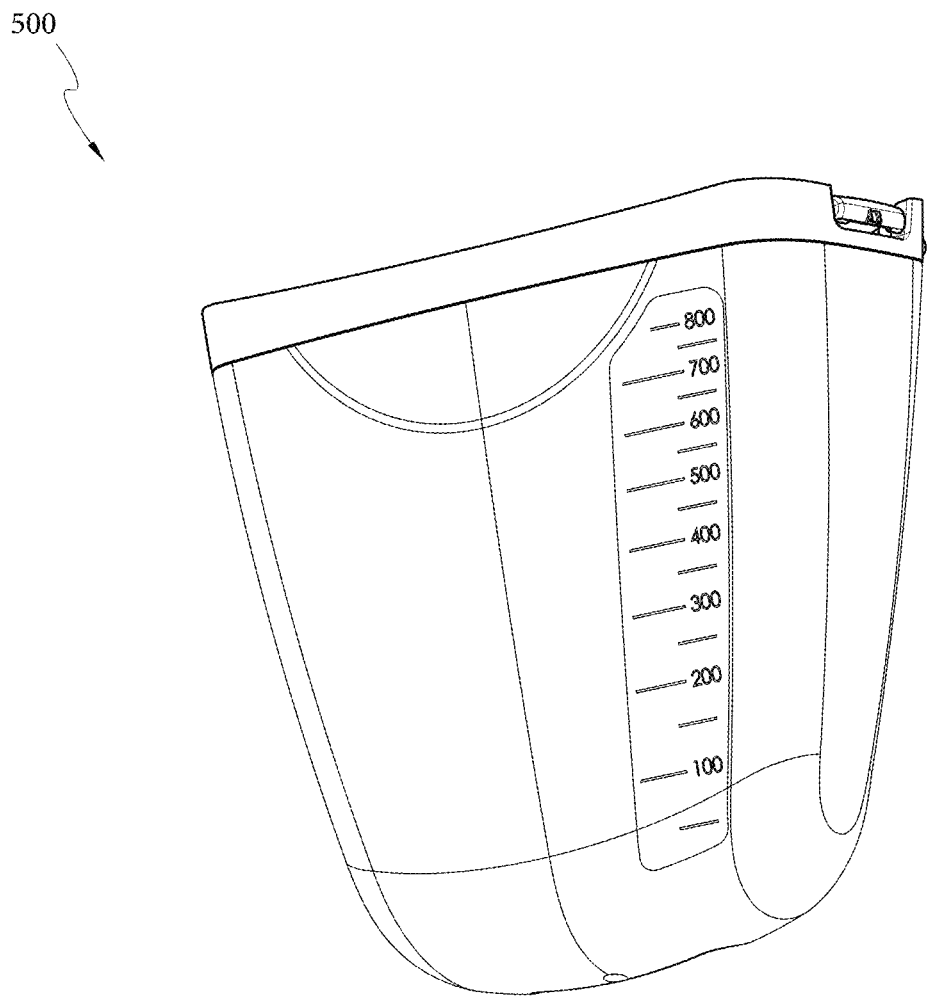
FIG. 5 illustrates a canister for use with a pump assembly, such as the pump assembly of FIG. 3.

The canister 220 is configured to hold fluid removed from the wound cavity 110. The canister 220 includes the one or more latches 221 for attaching the canister to the pump assembly 230. The canister 220 can include two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 230, such as during removal of the canister from the pump assembly 230. The canister 220 includes a substantially transparent window 216, which can also include graduations of volume. For example, the canister 220 has a fluid capacity of 300 mL and includes graduations of 50 mL, 100 mL, 150 mL, 200 mL, 250 mL, and 300 mL. Other aspects of the canister can hold a different volume of fluid and can include different graduation scale. For example, a canister 500 shown in FIG. 5 can be used in place of the canister 220 with the pump assembly 230, and the canister 500 has a 800 mL fluid capacity canister with 50 mL increment graduations from 50 mL to 800 mL. The canister 220 comprises a tubing channel 218 for connecting to the conduit 140. In some aspects, various of these features, such as the gripping portion 214, are omitted or various additional features are added to the canister 220. Any of the disclosed canisters may include or may omit a solidifier.

Figure 2B:
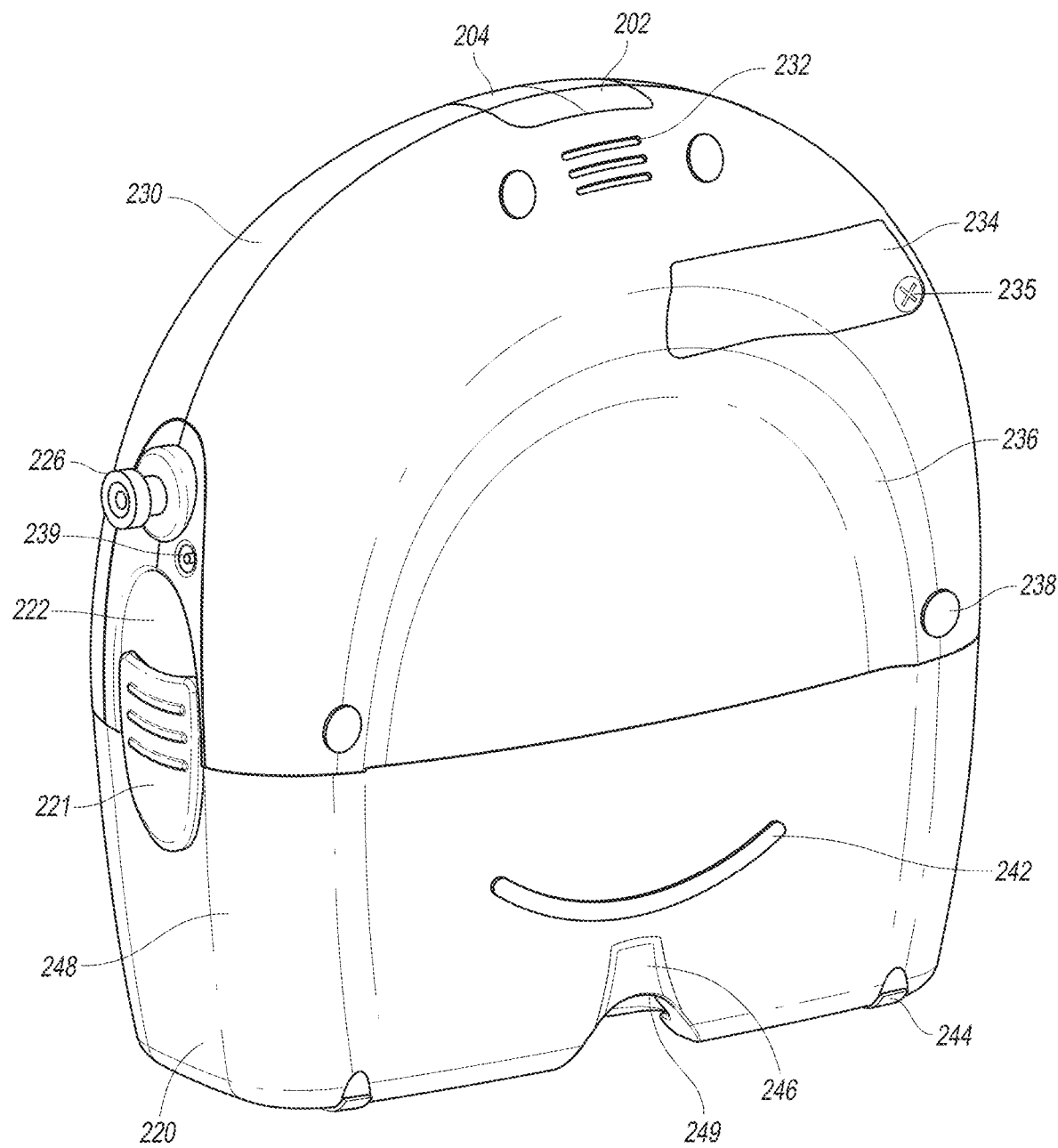

FIG. 2B illustrates a rear view of the pump assembly 230 and canister 220. The pump assembly 230 comprises a speaker port 232 for producing sound. The pump assembly 230 includes a filter access door 234 with a screw 235 for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some aspects, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. The kickstand 248 can be made out of an opaque material, such as plastic, or a transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
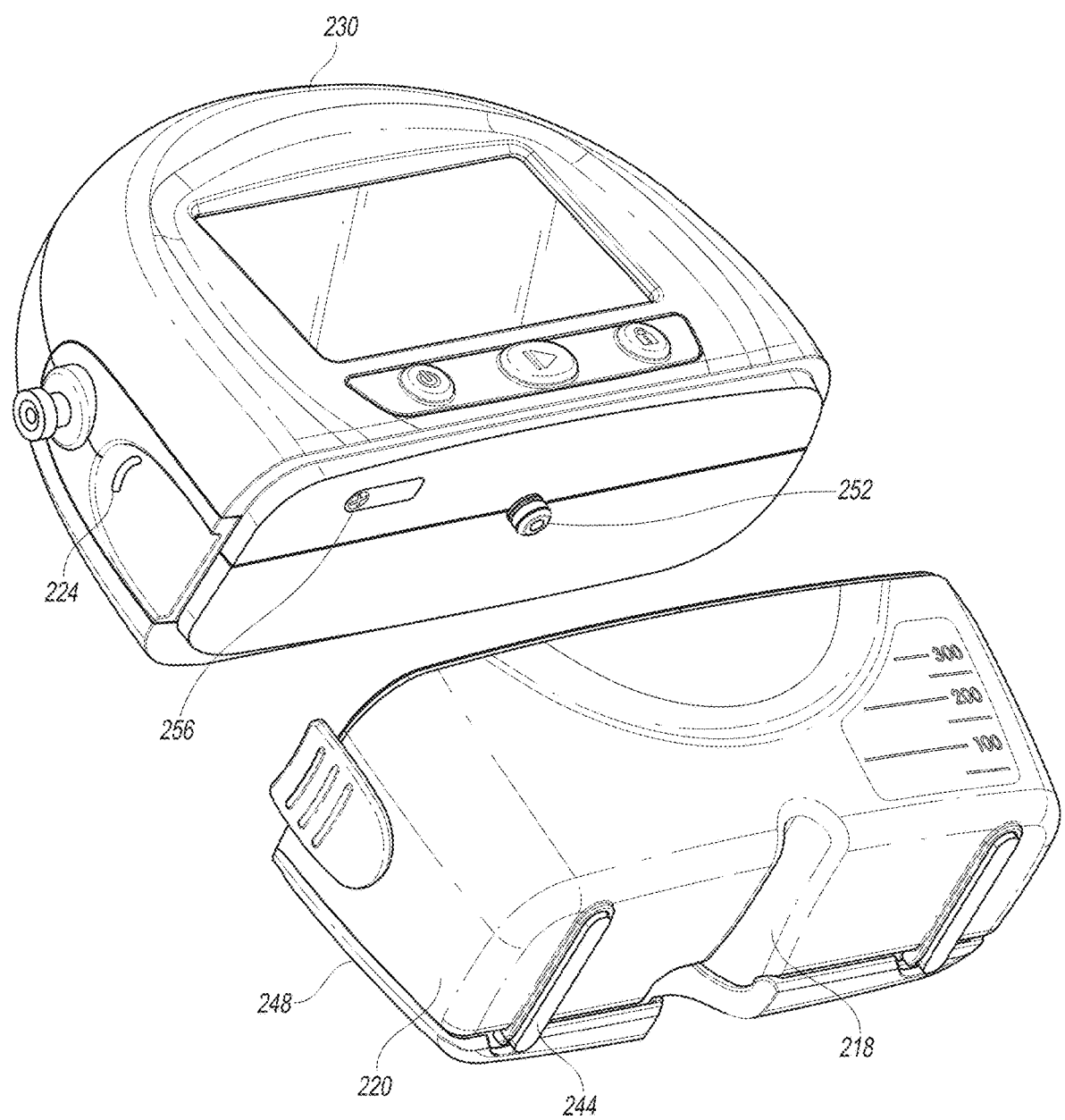

FIG. 2C illustrates a view of the pump assembly 230 separated from the canister 220. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 may include an access door 256 configured to allow access to one or more serial, parallel, or hybrid data transfer connector interfaces, such as USB, SD, Compact Disc (CD), DVD, Fire Wire, Thunderbolt, PCI Express, and the like. Additionally or alternatively, one or more serial, parallel, or hybrid data transfer connector interfaces may be accessed through the access door 234. The connector interfaces can be connector ports.

Figure 3:
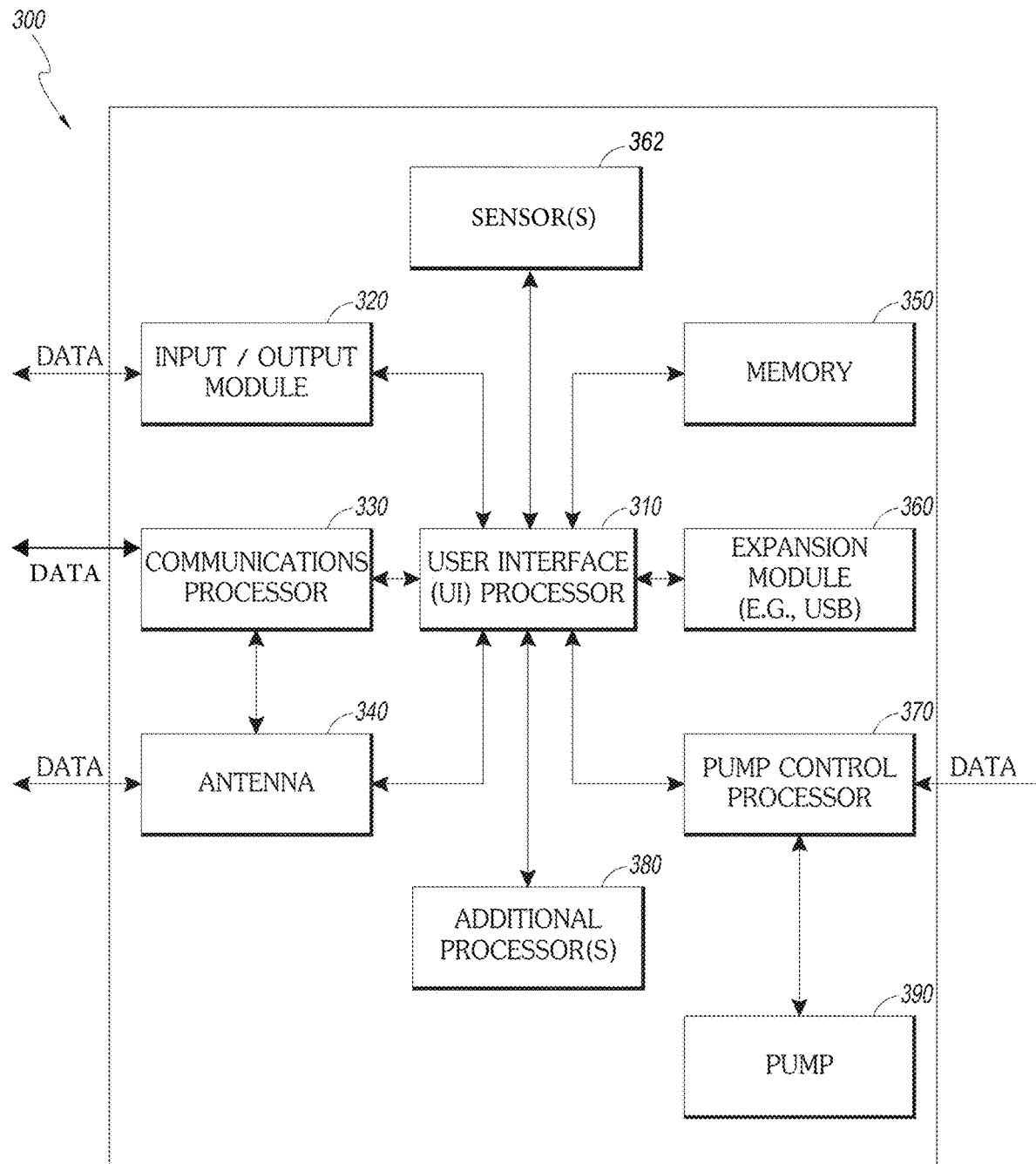
FIG. 3 illustrates an electrical component schematic of a pump assembly.

FIG. 3 illustrates an electrical component schematic of a pump assembly 300, such as the pump assembly 230. Electrical components can operate to accept user input, provide output to the user, operate the pump assembly and the TNP system, provide network connectivity, and so on. Electrical components can be mounted on one or more printed circuit boards (PCBs) that mechanically support and electrically connect electronic components using conductive tracks, pads and other features etched from copper sheets laminated onto a non-conductive substrate. Components, such as capacitors, resistors, or active devices, can be soldered on the PCBs or embedded in the substrate. PCBs can be single sided (one copper layer), double sided (two copper layers) or multi-layer (outer and inner layers), and conductors on different layers can be connected with vias. As is illustrated, the pump assembly can include multiple processors.

The pump assembly can comprise a user interface processor or controller 310 that can function as a main processor and be configured to operate one or more components for accepting user input and providing output to the user, such as the display 206, buttons 212, etc. Input to the pump assembly and output from the pump assembly can controlled by an input/output (I/O) module 320. For example, the I/O module 320 can receive data from one or more ports, such as serial, parallel, hybrid ports, and the like. The processor 310 also receives data from and provides data to one or more expansion modules 360, such as one or more USB ports, SD ports, CD drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, magnetoresistive random-access memory (MRAM), and the like.

The processor 310 can be a general purpose controller, such as a low-power processor, or an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (for example, processor for controlling the display 206, processor for controlling the buttons 212, etc.). The processor 310 can run a suitable operating system, such as a Linux, Windows CE, VxWorks, etc.

The processor 310 can communicate with and receive sensor data from one or more sensors 362. The one or more sensors 362 can include a pressure sensor, a flow rate sensor, an optical sensor, a magnetic field sensor, an inductance sensor, or the like. The sensor data from the one or more sensors 362 can be usable by the processor 310 to monitor one or more parameters indicative of a progress of therapy, a state of the wound, information about fluid from the wound, among other information. The one or more sensors 362 can be positioned in a housing of the pump assembly 300, proximate to a fluid flow path connecting the pump assembly 300 and a wound dressing, in or around a wound dressing being used in combination with the pump assembly 300, or at another suitable position to detect an activity of the pump assembly 300 or information indicative of therapy or a state of the wound.

The pump control processor 370 can be configured to control the operation of a pump 390, such as a negative pressure pump. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors (such as, of the one or more sensors 362), calculate the rate of fluid flow, and control the pump. The pump control processor 370 can control a pump motor so that a desired level of negative pressure is achieved in the wound cavity 110. The desired level of negative pressure can be pressure set or selected by the user. The pump control processor 370 can control the pump (for example, pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (for example, 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. The pump assembly can include a SIM card, and SIM-based positional information can be obtained.

The communications processor 330 can also be electrically coupled to one or more one or more serial, parallel, or hybrid data transfer connector interfaces through which the communications processor 330 can directly receive data or commands without receiving the data or commands through or from the processor 310. For instance, the data transfer connector interfaces can include one or more USB ports, SD ports, CD drives, DVD drives, Fire Wire ports, Thunderbolt ports, PCI Express ports, and the like.

The communications processor 330 can communicate information to the processor 310 and receive information from the processor 310. The communications processor 330 can include internal memory or can utilize memory 350. The communications processor 330 can be a low-power processor.

Using the connectivity provided by the communications processor 330, the device can upload any of the data stored, maintained, or tracked by the pump assembly. The device can also download various operational data, such as therapy selection and parameters, firmware and software patches and upgrades, and the like.

Figure 4:
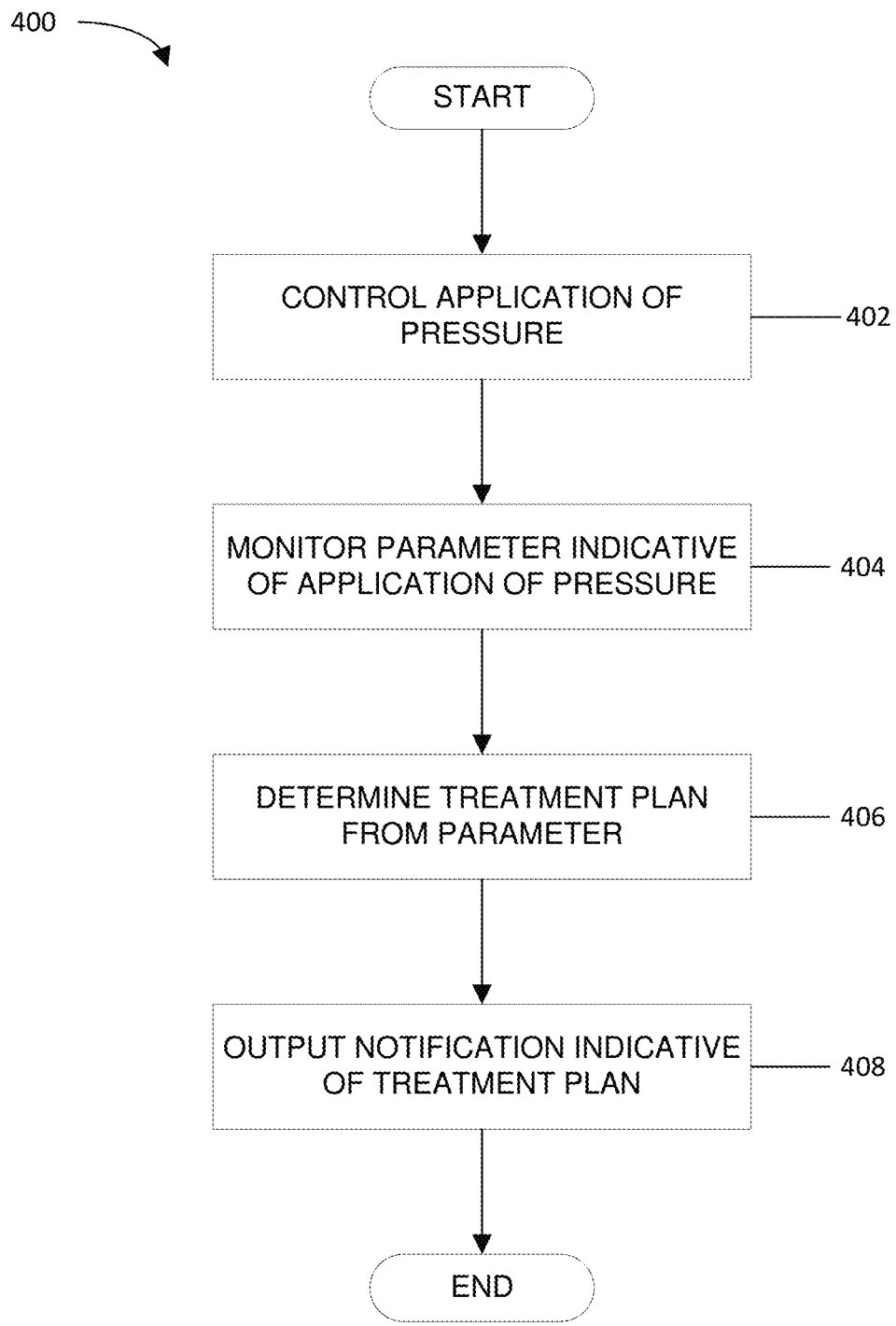
FIG. 4 illustrates a process for monitoring a state of a wound and determining a treatment plan.

FIG. 4 illustrates a process 400 for supporting treatment of a wound by automatically determining a treatment plan for the wound. The process 400 can applied to any one of pump assemblies described herein, other pump assemblies, or other wound treatment devices. The process 400 can advantageously, in certain aspects, provide information about the character of a wound or a progress of healing of the wound during wound therapy and be used to alert an individual to negative or positive developments for the wound and enable informed and timely decisions to be made about treatment.

At block 402, the application of negative pressure can be controlled. For example, the pump control processor 370 can control generation and application of negative pressure with the pump 390. The pressure can be provided as part of a wound therapy for treatment of a wound, and a wound dressing may be positioned over the wound and in fluidic communication with the pump 390 as described herein.

At block 404, the pump assembly can monitor one or more parameters that are indicative of negative pressure being provided to the wound dressing. The one or more parameters can include a pressure in a flow path connecting a wound dressing and the pump assembly, a flow rate in the flow path, a blockage in the flow path, a dressing fill rate or amount, a canister fill rate or amount, a duration of treatment with the pump assembly, a level of pump activity of the pump assembly, a depth of the wound, a fluid viscosity in the flow path, a granulation of tissue at the wound, a tissue tunneling at the wound, or other patient information, among other possibilities. The one or more parameters can be indicative of a progress of healing of a wound being treated with the wound dressing, as well as usable to monitor and forecast a release of fluid from the wound or healing of the wound during treatment. For example, the processor 310 can monitor the one or more parameters from sensor data collected by the one or more sensors 362 during provision of negative pressure with the pump 390, during wound therapy, or at other times.

At block 406, a treatment plan for the wound can be determined from the one or more parameters (for example, using one, two, three, four or more different parameters). The treatment plan can be determined from a comparison of (i) the one or more parameters or (ii) a change in the one or more parameters over time to a threshold, a parameter model, or a parameter pattern, among other possibilities. The threshold, the parameter model, or the parameter pattern can depend on patient or wound information (such as information provided by a caregiver like a wound size, depth, or color) or therapy device information (such as a canister size or therapy settings).

Figure 6A:
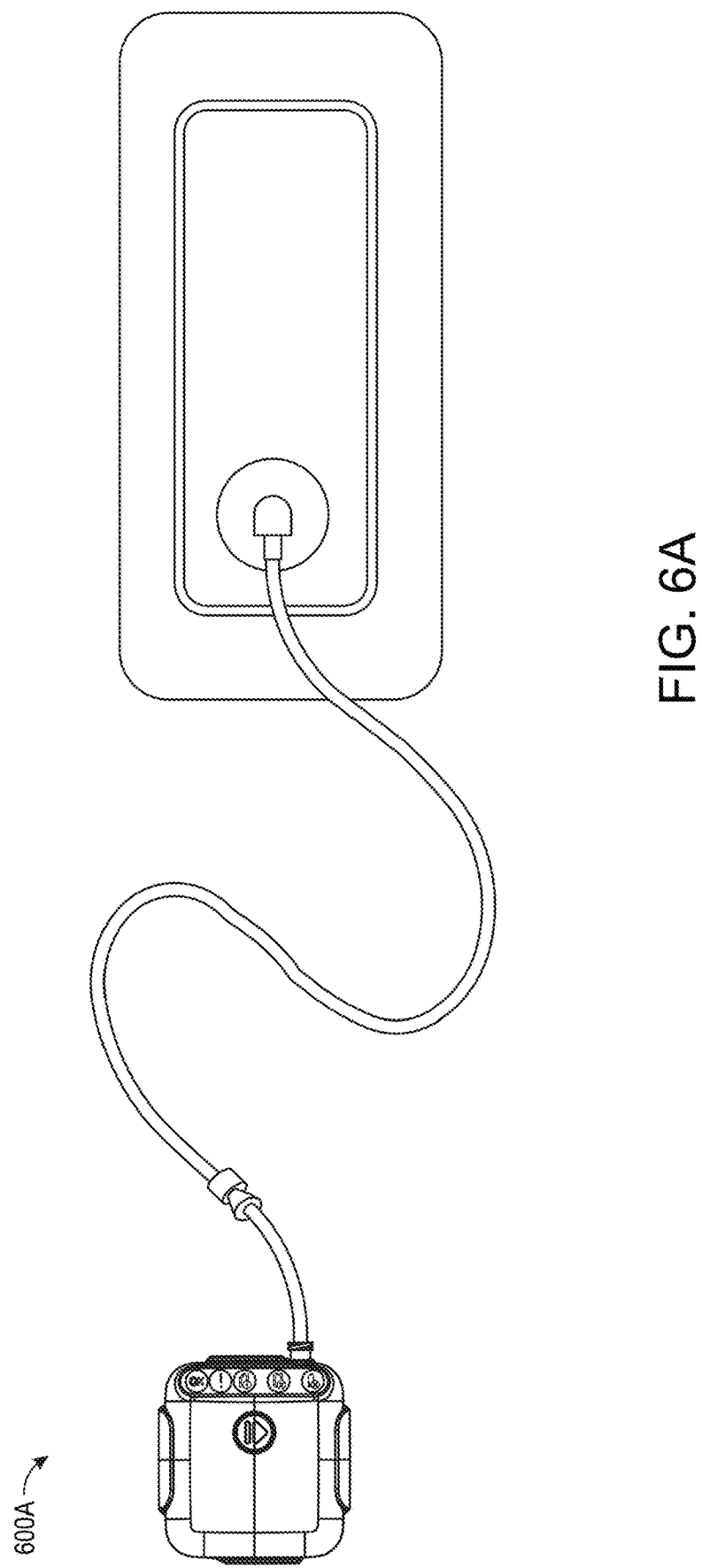
FIGS. 6A and 6B illustrate a canisterless pump assembly connected to different wound dressings.
Figure 6B:
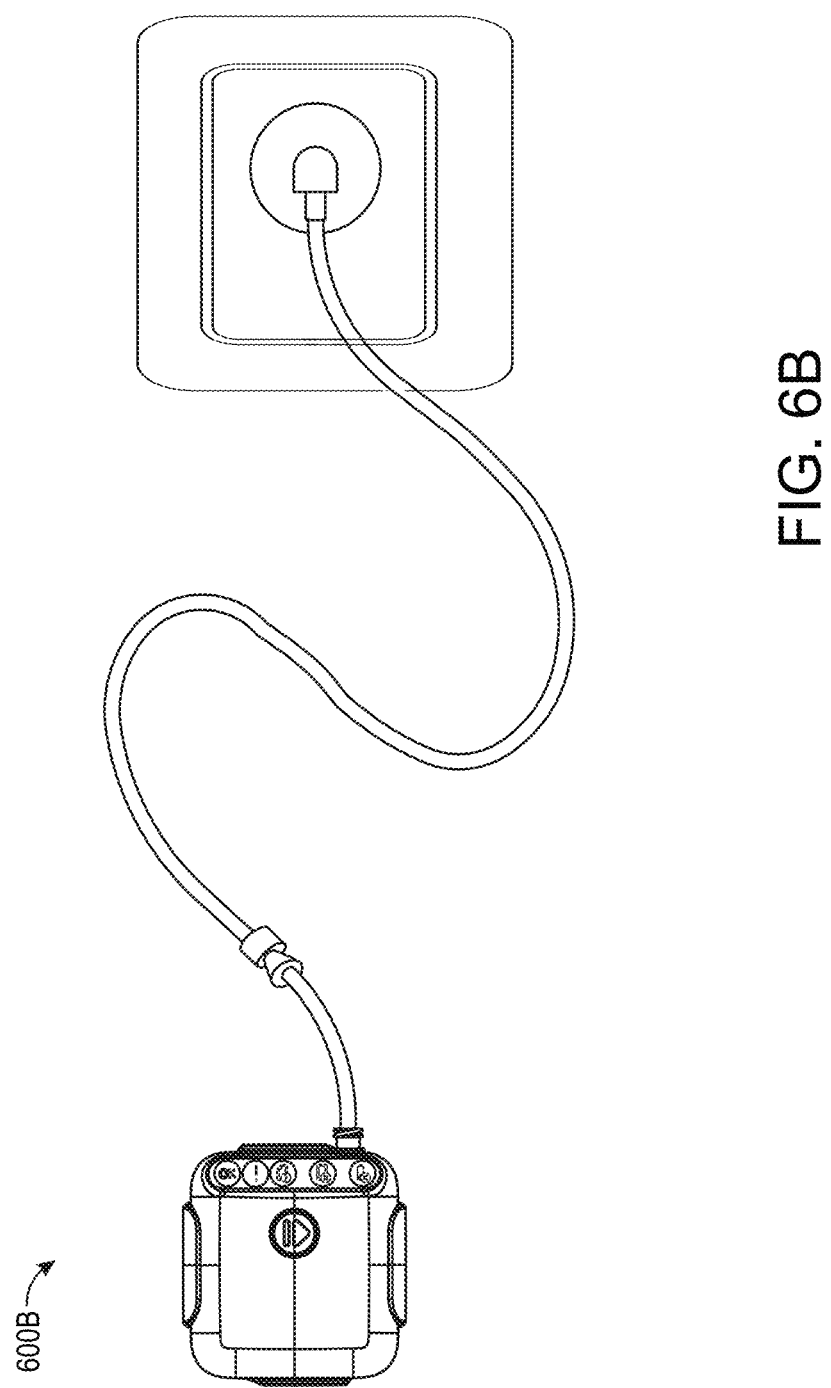
Figure 7:
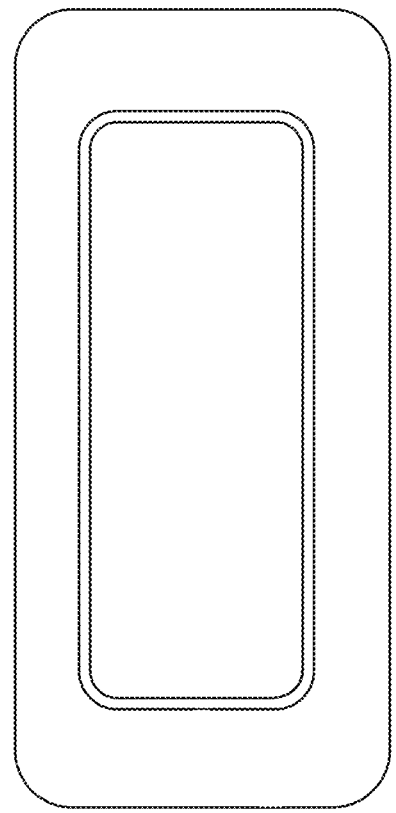
FIG. 7 illustrates a non-negative pressure therapy wound dressing.

The comparison, for instance, can be used to characterize a current condition of the wound or a change in the condition of the wound over time. When the wound is characterized to be healing or likely to expel less exudate, the treatment plan can include a positive progress suggestion, such as one or more of (i) change a canister size used in treating the wound, such as by decreasing the canister size from the canister 500 of FIG. 5 to the canister 220 of FIG. 2A, (ii) change a pressure source used in treating the wound, such as by decreasing a size or a power of the pressure source, (iii) change from treating the wound with a pump assembly and a canister, such as the pump assembly 230 and the canister 220 of FIG. 2A, to treating the wound with a canisterless treatment device, such as canisterless pump assembly systems 600A, 600B shown in FIG. 6A or 6B or a non-negative pressure wound dressing 700 shown in FIG. 7, (iv) change a wound dressing size used in treating the wound, such as by decreasing the wound dressing size from the size shown in FIG. 6A to the size shown in FIG. 6B, (v) discontinue further application of pressure to the wound with a pressure source, such as by transitioning from treating with the canisterless pump assembly system 600B of FIG. 6B to the non-negative pressure wound dressing shown 700 in FIG. 7, (vi) begin or stop using medical equipment other than a pump assembly along with use of the pump assembly to treat the wound, or (vii) change a treatment schedule or a pressure setting of a pump assembly when using the pump assembly to treat the wound, among other possibilities. When the wound is characterized to be not healing or likely to expel more exudate, the treatment plan can include an enhance treatment suggestion, such as one or more of (i) change a canister size used in treating the wound, such as by increasing the canister size from the canister 220 of FIG. 2A to the canister 500 of FIG. 5, (ii) change a pressure source used in treating the wound, such as by increasing a size or a power of the pressure source, (iii) change from treating the wound with a canisterless pump assembly, such as the canisterless pump assembly systems 600A, 600B shown in FIG. 6A or 6B, to treating the wound with a pump assembly and a canister, such as the pump assembly 230 and the canister 220 of FIG. 2A, (iv) change a wound dressing size used in treating the wound, such as by increasing the wound dressing size from the size shown in FIG. 6B to the size shown in FIG. 6A, (v) continue further application of pressure to the wound with a pressure source beyond a scheduled end time, (vi) begin or stop using medical equipment other than a pump assembly along with use of the pump assembly to treat the wound, or (viii) change a treatment schedule or a pressure setting of a pump assembly when using the pump assembly to treat the wound, among other possibilities. The treatment plan can indicate that an action may be desirably taken at a current time or at some future time so that plans or considerations in preparation for the action may be made. The processor 310 can, for example, determine the treatment plan from the one or more parameters.

In one example, where the one or more parameters can include the flow rate, a relatively higher flow rate can indicate a large amount of exudate collection while a relatively lower flow rate can indicate a smaller amount of exudate collection. As a result, the magnitude of the flow rate or the change in the rate over time may be used to determine an amount of exudate collection and a change or a trend in exudate collection from the wound. If the amount, change, or trend indicates that the wound is healing or less exudate is likely to be expelled from the wound (for instance, if the flow rate of fluid in the fluid flow path is below 20, 30, 40, 50, 60, 70, 80, or 100 mL/day), the treatment plan can include one or more positive progress suggestions. If the amount, change, or trend indicates that the wound is not healing or more exudate is likely to be expelled from the wound (for instance, if the flow rate of fluid in the fluid flow path is at least 20, 30, 40, 50, 60, 70, 80, or 100 mL/day), the treatment plan can include one or more enhanced treatment suggestions.

In another example, where the one or more parameters can include the dressing fill rate or the canister fill rate, a relatively higher fill rate can indicate a large amount of exudate collection while a relatively lower fill amount can indicate a smaller amount of exudate collection. As a result, the magnitude of the fill rate or the change in the fill rate over time may be used to determine an amount of exudate collection and a change or a trend in exudate collection from the wound. If the amount, change, or trend indicates that the wound is healing or less exudate is likely to be expelled from the wound (for instance, if the fill rate is below 20, 30, 40, 50, 60, 70, 80, or 100 mL/day or 1 or 2 dressing or canister changes are expected to be made per week), the treatment plan can include one or more positive progress suggestions. If the amount, change, or trend indicates that the wound is not healing or more exudate is likely to be expelled from the wound (for instance, if the fill rate is at least 20, 30, 40, 50, 60, 70, 80, or 100 mL/day or at least 3 dressing or canister changes are expected to be made per week), the treatment plan can include one or more enhanced treatment suggestions.

As yet another example, where the one or more parameters can include the level of pump activity, a relatively higher level of activity of a fixed speed pump can indicate a large amount of exudate collection while a relatively lower level of activity of the fixed speed pump can indicate a smaller amount of exudate collection. As a result, the magnitude of the speed of the pump or the change in the magnitude of the speed of the pump over time may be used to determine an amount of exudate collection and a change or a trend in exudate collection from the wound. If the amount, change, or trend indicates that the wound is healing or less exudate is likely to be expelled from the wound, the treatment plan can include one or more positive progress suggestions. If the amount, change, or trend indicates that the wound is not healing or more exudate is likely to be expelled from the wound, the treatment plan can include one or more enhanced treatment suggestions.

In a further example, where the one or more parameters can include the depth of the wound, a relatively deeper wound can indicate a large amount of exudate collection while a relatively shallower wound can indicate a smaller amount of exudate collection. As a result, the depth of the wound or the change in the depth of the wound over time may be used to determine an amount of exudate collection and a change or a trend in exudate collection from the wound. If the amount, change, or trend indicates that the wound is healing or less exudate is likely to be expelled from the wound (for instance, if the wound depth is determined to be less than 1.0, 1.2, 1.4, 1.5, 1.6, 1.8, 2.0, 2.2, 2.4, 2.5, 2.6, 2.8, or 3.0 cm), the treatment plan can include one or more positive progress suggestions. If the amount, change, or trend indicates that the wound is not healing or more exudate is likely to be expelled from the wound (for instance, if the wound depth is determined to be at least 1.0, 1.2, 1.4, 1.5, 1.6, 1.8, 2.0, 2.2, 2.4, 2.5, 2.6, 2.8, or 3.0 cm), the treatment plan can include one or more enhanced treatment suggestions.

Information relating to the beginning and duration of therapy can be stored in memory, such as the memory 350. Likewise, information about the frequency and amount of exudate collected can be stored in memory, such as the memory 350. Such information can be used in preparing an initial treatment plan and then updating the treatment plan. For instance, based on the starting date of the treatment and other information such as about a patient or their wound (such as, a patient age, weight, height, gender, medical history, expected patient activity level, location of wound, therapy settings, or the like), an initial treatment plan can be prepared. This initial treatment plan can then be adjusted based on the comparison with the one or more parameters.

At block 408, the pump assembly can output a notification indicative of the treatment plan. The notification can include an identification of one or more positive progress suggestions, one or more enhanced treatment suggestions, or denote an availability of the treatment plan determined from the one or more parameters (such as, for review by a caregiver rather than a patient so that the patient may be made aware that attention is desired but is not directly informed about details of the treatment plan). The notification can be output for presentation, such as via a display like the display 206 of FIG. 2A, an indicator light of the pump assembly like the indicators 202 or 204 of FIG. 2A, a speaker of the pump assembly, or a tactile indicator of the pump assembly. The notification may be output for storage in a memory, such as the memory 350, or output via a communication interface to another electric device, such as to a computer, a server, or a smartphone via a computer network or other communication.

Figure 8A:
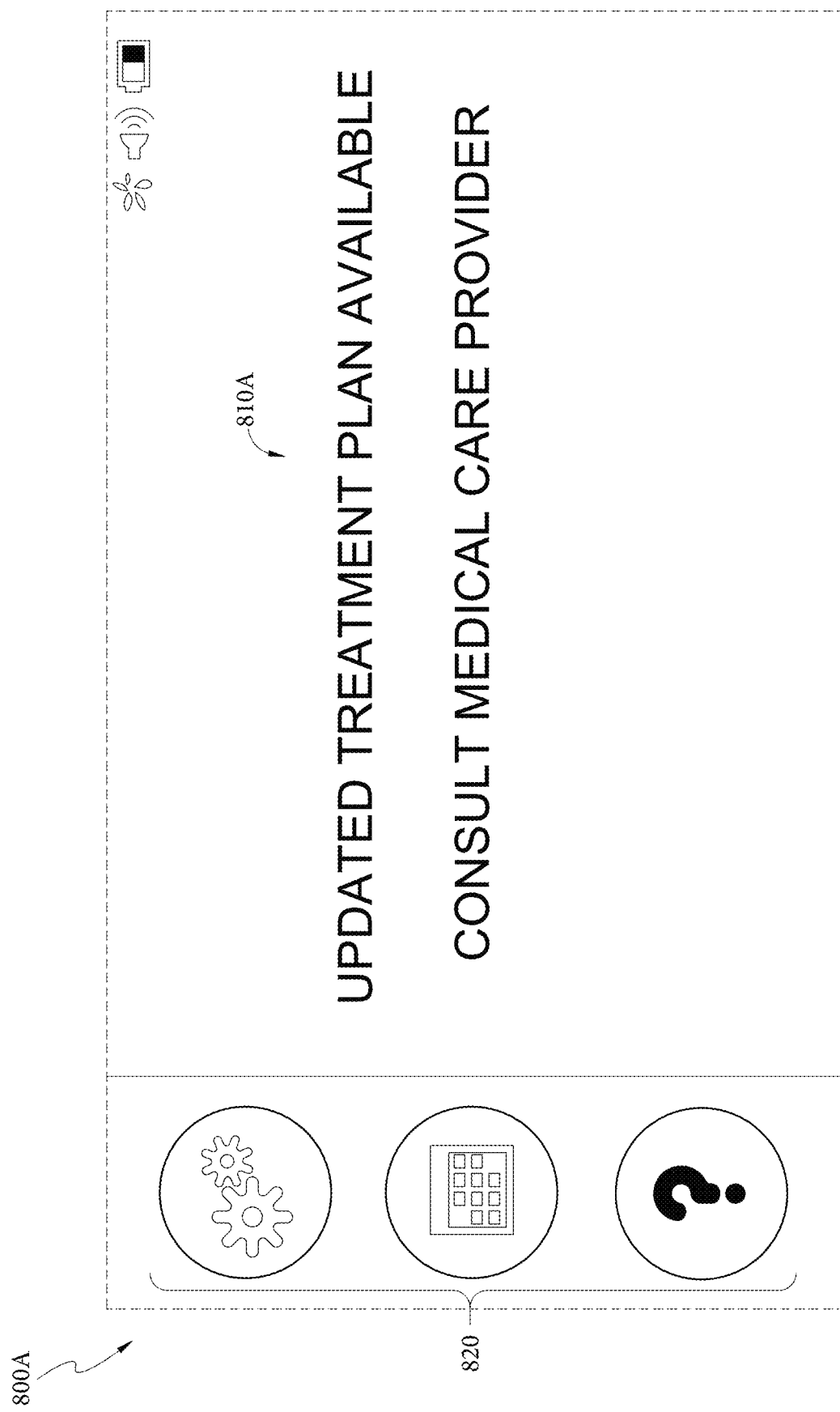
FIGS. 8A and 8B illustrate notification screens presentable in a wound therapy system.

FIG. 8A illustrates a notification screen 800A. The notification screen 800A can be used to display the notification of the treatment plan as described with reference to block 408 of the process 400. The notification screen 800A can present a treatment plan message 810A, which may indicate that the pump assembly has determined a treatment plan for display. The treatment plan message 810A may notably not indicate what treatment plan has been determined, but may instead indicate to consult with a caregiver. The notification screen 800A can include a menu 820 for navigating to other screens, such as for controlling application of pressure.

Figure 8B:
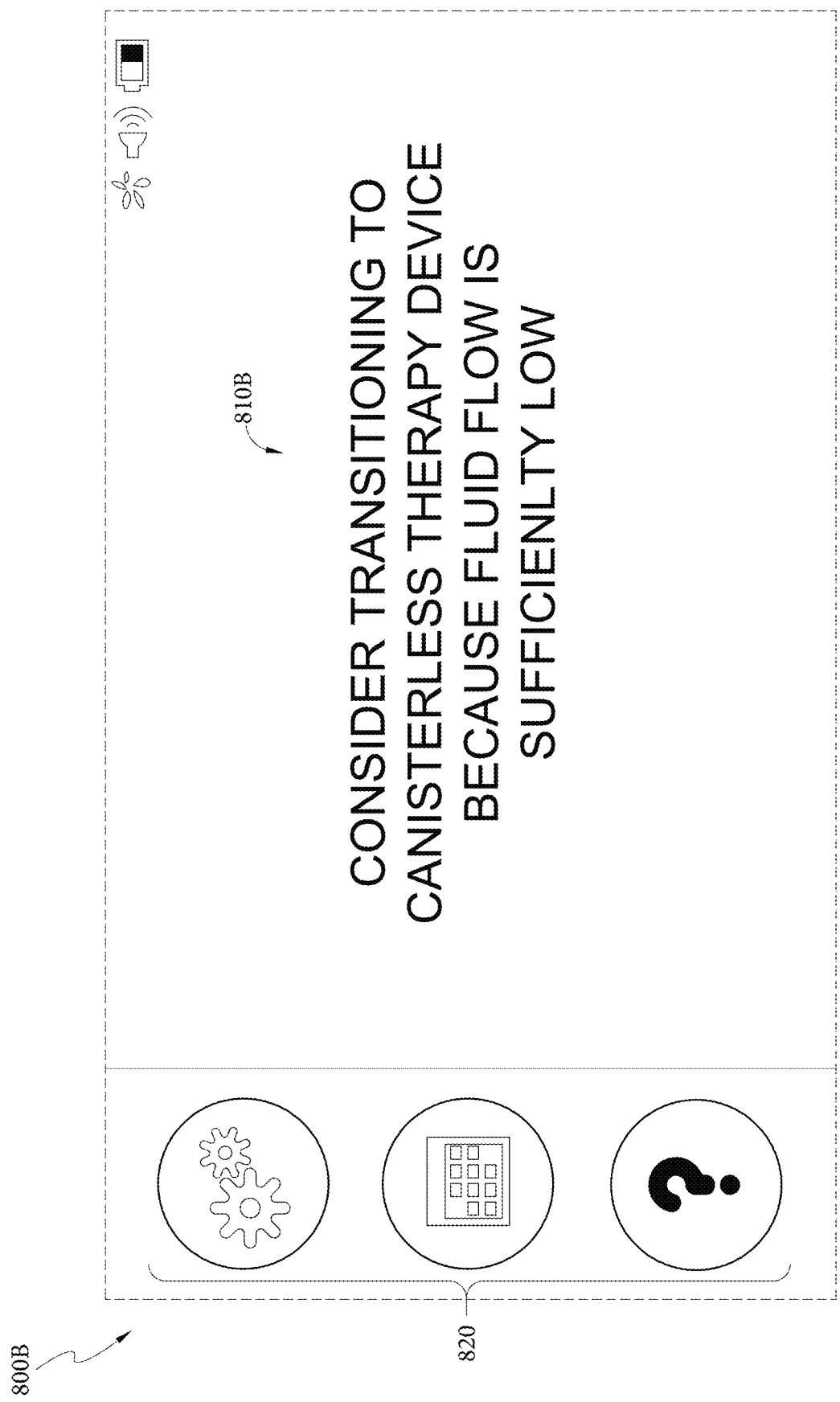

FIG. 8B illustrates a notification screen 800B. The notification screen 800B can be used to display the notification of the treatment plan as described with reference to block 408 of the process 400. The notification screen 800B can present a progress message 810B, which may provide a positive progress suggestion, such as that treatment can transition from use of a pump assembly and a canister to use of a canisterless treatment device. The progress message 810B can moreover provide one or more reasons for the positive progress suggestion, such as an indication that a fluid flow rate has satisfied a threshold for use of the canisterless treatment device.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for applying negative pressure to a wound, the apparatus comprising:
   a negative pressure source configured to provide negative pressure via a fluid flow path to the wound covered by a wound dressing positioned over the wound; and
   a controller configured to:
      cause the negative pressure source to aspirate fluid from the wound and cause at least some of the fluid extracted from the wound to be stored in a canister positioned in the fluid flow path,
      monitor an amount of fluid aspirated from the wound over a period of time,
      based on the amount of fluid aspirated from the wound, determine that the wound is treatable with a canisterless wound therapy that does not utilize any canister, and
      output for presentation to a user a notification indicating that the wound is treatable with the canisterless wound therapy.

2. The apparatus of claim 1, wherein the controller is configured to determine that the wound is treatable with the canisterless wound therapy by monitoring a rate of flow in the fluid flow path over the period of time.

3. The apparatus of claim 1, wherein the controller is configured to determine that the wound is treatable with the canisterless wound therapy by monitoring a number of canister changes over the period of time.

4. The apparatus of claim 3, wherein the controller is further configured to determine from the number of canister changes over the period of time whether the wound is healing.

5. The apparatus of claim 4, wherein the controller is configured to determine whether the wound is healing by comparing the number of canister changes to a predetermined value, and wherein the controller is configured to:
   determine that the wound is healing in response to the number of canister changes being less than the predetermined value; and
   determine that the wound is not healing in response to the number of canister changes being equal to or greater than the predetermined value.

6. The apparatus of claim 5, wherein the period of time comprises a week and the predetermined value comprises 3 canister changes per week.

7. The apparatus of claim 1, further comprising a sensor configured to monitor the amount of fluid aspirated from the wound.

8. The apparatus of claim 1, wherein the controller is configured to determine a forecast of the amount of fluid aspirated from the wound and output the forecast for presentation to the user.

9. The apparatus of claim 1, further comprising a display configured to present the notification.

10. The apparatus of claim 1, wherein the controller is configured to determine that the wound is treatable with the canisterless wound therapy further using information received about a patient that has the wound.

11. A kit comprising the apparatus of claim 1 and a canisterless wound therapy apparatus configured to provide the canisterless wound therapy, the canisterless wound therapy apparatus comprising an accompanying pressure source and being configured to operate in combination with an accompanying wound dressing that has a different fluid capacity than the wound dressing.

12. A method of operating a negative pressure wound therapy apparatus, the method comprising:
   causing a negative pressure source to aspirate fluid from a wound covered by a wound dressing and causing at least some of the fluid extracted from the wound to be stored in a canister positioned in a fluid flow path connecting the negative pressure source to the wound;
   monitoring an amount of fluid aspirated from the wound over a period of time;
   based on the amount of fluid aspirated from the wound, determining that the wound is treatable with a canisterless wound therapy that does not utilize any canister; and
   responsive to determining that the wound is treatable with the canisterless wound therapy, outputting for presentation to a user a notification indicating that the wound is treatable with the canisterless wound therapy,
   wherein the method is performed by a controller of the negative pressure wound therapy apparatus.

13. The method of claim 12, wherein determining that the wound is treatable with the canisterless wound therapy is performed by monitoring a rate of flow in the fluid flow path over the period of time.

14. The method of claim 12, wherein determining that the wound is treatable with the canisterless wound therapy is performed by monitoring a number of canister changes over the period of time.

15. The method of claim 14, further comprising determining from the number of canister changes over the period of time whether the wound is healing.

16. The method of claim 15, wherein determining whether the wound is healing by comparing the number of canister changes to a predetermined value, and wherein the method further comprises:
   at a first time, determining that the wound is healing responsive to determining that the number of canister changes is less than the predetermined value; and
   at a second time, determining that the wound is not healing responsive to determining that the number of canister changes is equal to or greater than the predetermined value.

17. The method of claim 16, wherein the period of time comprises a week and the predetermined value comprises 3 canister changes per week.

18. The method of claim 12, further comprising determining a forecast of the amount of fluid aspirated from the wound and outputting the forecast for presentation to the user.

19. The method of claim 12, wherein the notification is visually presented to the user.

20. The method of claim 12, wherein determining that the wound is treatable with the canisterless wound therapy is performed further using information received about a patient that has the wound.

* * * * *